United States Patent [19]

Weigert et al.

[11] 4,326,538
[45] Apr. 27, 1982

[54] METHOD AND APPARATUS FOR ANALYSIS OF ESSENTIALLY PERIODIC SIGNAL SEQUENCES

[75] Inventors: Kurt Weigert, Nuremberg; Claudius Molz, Erlangen, both of Fed. Rep. of Germany

[73] Assignee: Siemens Aktiengesellschaft, Berlin & Munich, Fed. Rep. of Germany

[21] Appl. No.: 138,709

[22] Filed: Apr. 9, 1980

[30] Foreign Application Priority Data

Apr. 20, 1979 [DE] Fed. Rep. of Germany ....... 2916067

[51] Int. Cl.³ .............................................. A61B 5/04
[52] U.S. Cl. .................................................. 128/702
[58] Field of Search ............... 128/696, 702, 703, 706, 128/708

[56] References Cited

U.S. PATENT DOCUMENTS

| | | | |
|---|---|---|---|
| 2,492,617 | 12/1949 | Boland et al. | 128/706 |
| 3,438,367 | 4/1969 | Karsh et al. | 128/702 |
| 3,518,983 | 7/1970 | Jorgensen | 128/702 |
| 3,618,593 | 11/1971 | Nachev et al. | 128/702 |
| 3,902,479 | 9/1975 | Chaumet | 128/703 |
| 3,968,431 | 7/1976 | Ekstrom | 128/706 |
| 3,978,856 | 9/1976 | Michel | 128/703 |

*Primary Examiner*—William E. Kamm
*Attorney, Agent, or Firm*—Hill, Van Santen, Steadman, Chiara & Simpson

[57] ABSTRACT

In automatic EKG-analysis, for example, the occurrence of signals, such as regular QRS-complex or also extrasystoles, is monitored in adjustable time intervals. However, it also happens that regular signal complexes in a signal sequence are lacking. In accordance with an exemplary embodiment, for the recognition and display of missing individual events in the essentially periodic signal sequence corresponding to the mean signal frequency, an adjustable measuring voltage, proportional to the signal period duration, is compared with the mean value formed from the measuring voltage summed up in the preceding signal period, whereby, upon exceeding the comparison voltage value, a count signal is triggered. In this manner, asystolias, or so-called "missed beats" of the EKG can be ascertained, while compensatory pauses after extrasystoles are eliminated.

18 Claims, 2 Drawing Figures

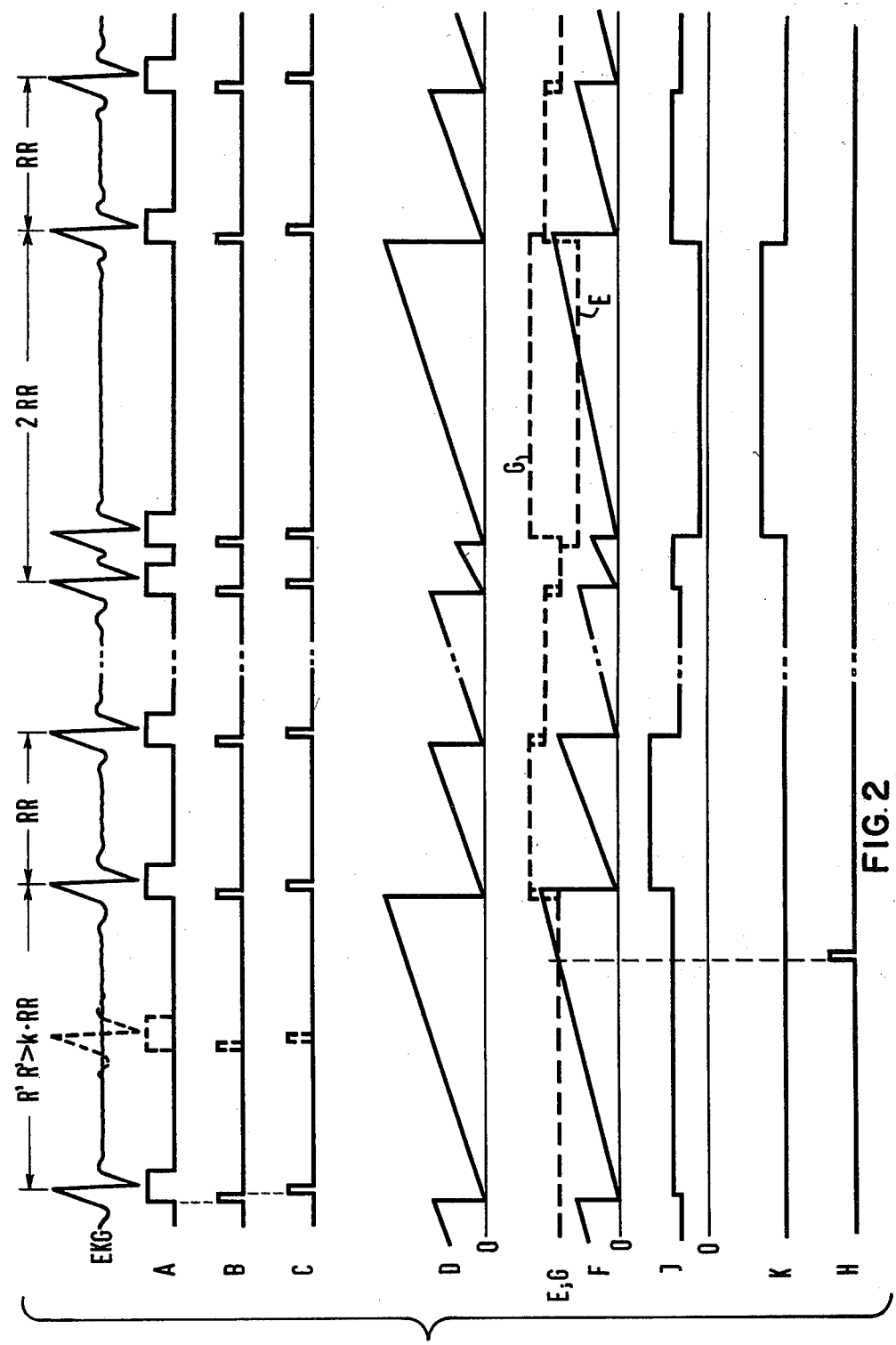

METHOD AND APPARATUS FOR ANALYSIS OF ESSENTIALLY PERIODIC SIGNAL SEQUENCES

BACKGROUND OF THE INVENTION

The invention relates to a method for the analysis of essentially periodic signal sequences; in particular, physiological signals, such as EKG or the like, as well as relating to an apparatus for carrying out this method.

In the analysis of essentially periodic signal sequences, generally significant signal events (or occurrences) are employed for the purpose of generating trigger signals. The latter are then analyzed with regard to period, or frequency, respectively, of the significant events. In addition, the occurrence of extraordinary events in the periodic sequence of normal events is also generally of interest, since the latter influence, in particular, directly, the frequency measurement (or test) result.

Particularly in the analysis of physiological signal waveforms; for example, an electrocardiogram, in addition to the frequency measurement on the basis of the significant signal events, also the actual structure analysis of the signals receives general consideration. From the chronological progression of the occurrence of extrasystoles, for example, the medical practitioner can derive diagnostic information. Therefore, in the state of the art, it is customary to monitor the interval between the normal QRS-complexes for extrasystoles. Known electromedical apparatus operate with constantly specifiable (or predeterminable) time intervals in which the occurrence of extrasystoles in the EKG is detected and classified.

Information can also be derived from the omission of a normal event in an essentially periodic signal sequence. Specifically, in the EKG-analysis technology, in the case of lack of a normal QRS-complex, one speaks of a so-called asystolia, or "missed beat". In the case of EKG-recording on the viewing screen of an oscilloscope or on the strip chart of a cardiograh, such asystolias or "missed beats" can indeed be immediately recognized by the medical practitioner as anomalies; however, in the case of automatic analysis of EKG-curves, they are not readily recognized and evaluated as such.

SUMMARY OF THE INVENTION

Accordingly, the object underlying the invention consists in disclosing a method and an apparatus with which the automatic analysis of essentially periodic signal sequences is improved. In particular, for the EKG-analysis technology, the possibility is to be provided for recording sporadically occurring (or isolated) asystolias or the failure of individual beats independently of the mean heart rate (or frequency).

In accordance with the invention, the object is achieved in that, for the recognition and display of lacking individual events in the essentially periodic signal sequence corresponding to the mean heart rate (or frequency), an adjustable measuring voltage, proportional to the signal period duration, is compared with the mean value from the measuring voltage summed up in the preceding signal period, whereby, upon exceeding the comparison voltage value, a count pulse is released (or triggered).

Thus, in the method according to the invention, a concomitant comparison voltage value is defined by the preceding signal period. The increasing time-proportional measuring voltage in the currently occurring signal period can then be so adjusted that a count pulse is triggered only upon exceeding an interval which surpasses the mean event interval by a specific multiplication factor. In this way an asystolia or a "missed beat" can be directly displayed in the case of EKG-analysis. In an advantageous embodiment, the measuring voltage, in addition, is further compared with an adjustable constant voltage, so that the count signal is generated even when a maximum specifiable (or predeterminable) time interval is exceeded. This time interval preferably amounts to two seconds (2 s), since, in the case of an EKG, an RR-interval greater than two seconds (2 s) is to be interpreted as pathological in every instance.

In a further development of the invention, also such event pauses, which are brought about solely due to a prematurely occurring significant event, can be recognized by means of comparison of the measuring voltage with the mean value of the comparison voltage, which mean value has been correspondingly raised by the degree of prematureness. Accordingly, in the EKG-analysis, compensatory pauses due to prematurely occurring extrasystoles can be distinguished from genuine asystolias or "missed beats".

An apparatus for carrying out the inventive method exhibits, in its circuit arrangement, a measuring voltage summer (or analog adder), a mean value formation member, a measuring voltage memory, and at least one comparator. Preferably, however, in the practical embodiment for the purpose of automatic EKG-analysis, three comparators are present, so that the display of an asystolia or ("missed beat") is possible upon exceeding a mean RR-interval (said mean RR-interval being exceeded by a predeterminable factor), in the case of a specified maximum interval, and so that simultaneously compensatory pauses after extrasystoles are recognized. The period-proportional measuring voltage is here formed, in a manner known per se, by a capacitor, chargeable by a constant current source, said capacitor serving as measuring voltage summer (or analog adder), which is discharged upon occurrence of a significant signal event, respectively. In this manner a sawtooth voltage corresponding to the signal intervals is generated. However, the level (or effective output amplitude) of this sawtooth voltage is adjustable for a mean event interval via voltage dividers corresponding to a specifiable (or predeterminable) multiplication factor.

Further advantages and details of the invention shall be apparent from the following detailed description of an exemplary embodiment on the basis of the accompanying sheets of drawings; and other objects, features and advantages will be apparent from this detailed disclosure and from the appended claims.

BRIEF DESCRIPTION OF THE DRAWINGS

FIG. 2 illustrates an exemplary input waveform, and shows in relation thereto pulse diagrams of the voltages occurring at the circuit points indicated by corresponding letters A–H, J and K in FIG. 1.

DETAILED DESCRIPTION

Figure 1:
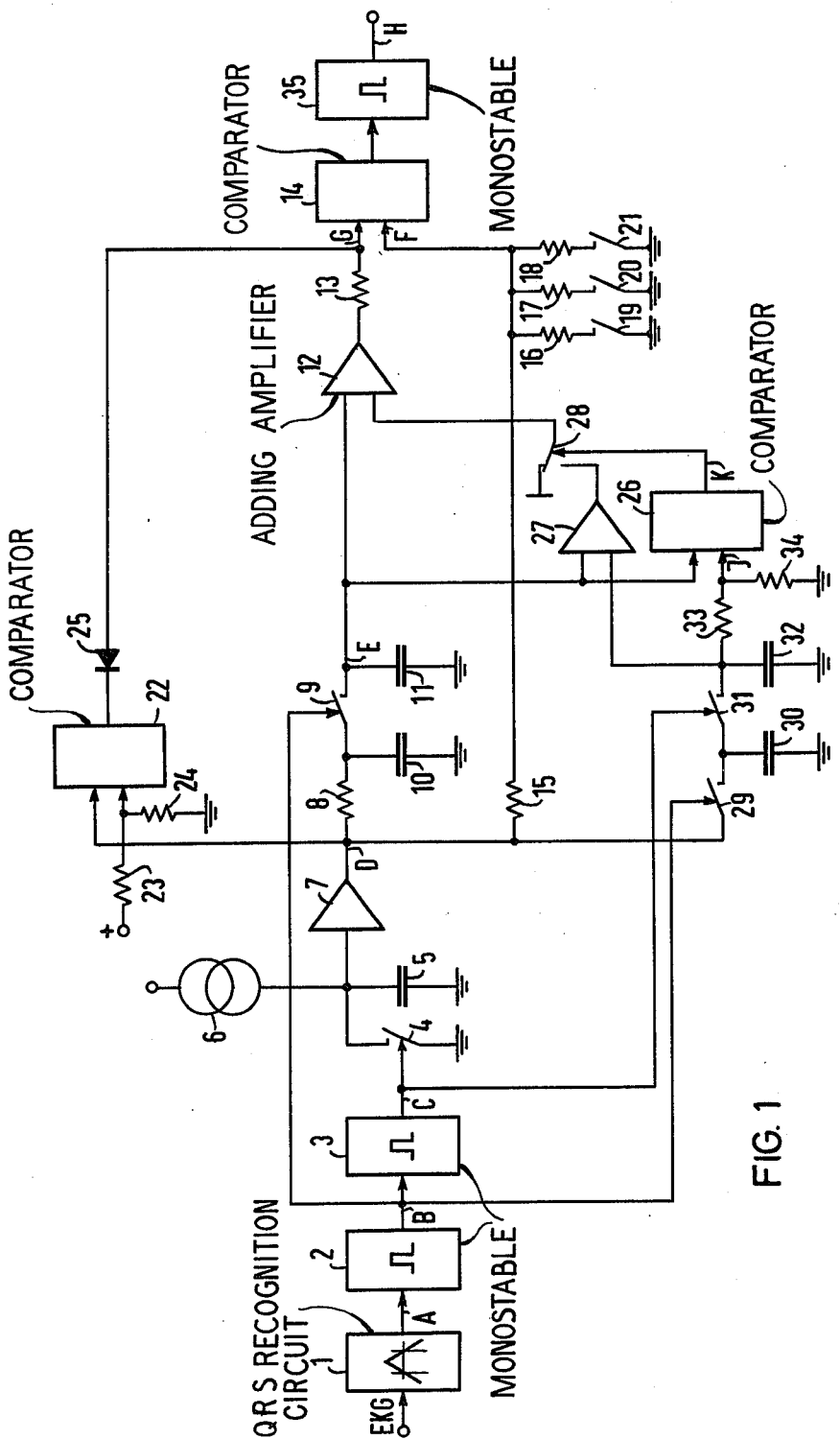
FIG. 1 illustrates an inventive circuit arrangement.

In FIG. 1 an EKG signal is fed into a circuit arrangement. The circuit arrangement consists of a component 1 for QRS-recognition with which, in the case of QRS-complexes exceeding a specific threshold and signal width, rectangular pulses are formed. Connected to the output side of the recognition circuit 1 are two monostable multivibrators 2 and 3, which generate correspondingly defined trigger pulses. In the circuit a capacitor 5 of suitable capacitance is charged by a current constant source 6. The voltage at the capacitor 5 thereby increases in a linear fashion with the time. Via a switch 4, which is connected across the terminals of the capacitor, which switch is controlled (or operated) by the trigger pulses of the monostable 3, the capacitor 5 is quickly discharged in each instance of an occurrence of a cardiac action. In this manner, a period-proportional sawtooth voltage results at the capacitor 5. Via an isolating (or buffer) amplifier 7, the sawtooth voltage reaches a low pass filter formed from a resistance 8 and a capacitor 10. This RC-network forms, in each instance, the mean value from the sawtooth-shaped input voltage. The mean value is stored, in the case of every cardiac action, in a sample-and-hold-circuit. This sample-and-hold-circuit basically consists of a switch 9, which is controlled by the first monostable 2, and a capacitor 11 as a storage member.

The voltage level stored in the sample and hold circuit 9, 11, reaches the input of a first comparator 14 via an adding amplifier 12, and a resistance 13. The saw-tooth-shaped voltage of the capacitor 5 reaches the second input of the comparator 14 via a selected voltage divider formed by resistances 15 through 18. The resistances 16 through 18 are here connected to be selectively activated to determine the transmission ratio of the voltage divider by means of associated switches 19 through 21. Thus, dependent upon the closure of switches 19, 20 and 21, the sawtooth voltage is attenuated in a predeterminable ratio. If the attenuated sawtooth voltage becomes greater than the stored mean value, the comparator 14 delivers an output signal to a monostable multivibrator 35 which triggers a count pulse for the purpose of further processing.

Thus, the output sawtooth measuring or reference voltage can be adjusted through the switching into the circuit of the resistances 16 through 18. In this manner it can be determined according to which multiplication factor k (k>1) of the mean RR-interval the comparator 14 switches over. For example, the voltage dividers 15-18 are so selected that the factors are k=1.6; 2.6, or 3.6. The multiplication factor k, determined by the selected voltage divider 15 through 18, is here independent of the heart rate (or frequency).

In a second comparator 22, the sawtooth-shaped voltage of the capacitor 5 is compared with a fixed voltage value which is determined by a voltage divider formed from resistances 23 and 24. If the sawtooth voltage exceeds the voltage value thereby preselected, then the comparator 22 switches over, whereby, via an output-connected diode 25, the input of the first comparator 14 is connected to negative potential, and the comparator 14 delivers a switching signal to monostable 35 so that a count pulse is triggered. With such a measure, it is achieved that, subsequent to expiration of a maximum time interval following a last cardiac action, a count pulse for an asystolia or "missed beat" is triggered. Such a time interval amounts, for example, to two seconds (2 s), since, for medical reasons, an RR-interval greater than two seconds (2 s) is absolutely to be interpreted as pathological.

In a third comparator 26 the mean value voltage of the sample and hold circuit 9, 11, is now compared with the peak value of the sawtooth-shaped voltage of the capacitor 5. The peak value of this sawtooth voltage is stored via two sample and hold circuits formed from the capacitors 30 and 32 with associated switches 29 and 31. The switches 29 and 31 are operated (or controlled) by the first and second monostables 2 and 3. These stored values reach the second input of the comparator 26 via the voltage divider formed from the resistances 33 and 34. An output signal of the comparator 26 effects a changeover switching of a switch 28 which is connected with the output of an amplifier 27. In the case of a changeover of switch 28, an additional bias voltage from the amplifier 27 is connected to the adding amplifier 12 which is connected with the first comparator 14. This bias voltage corresponds to the time difference between the mean (or average) heart period and the time of a prematurely occurring cardiac action. The output voltage of the adding amplifier 12 is hereby raised precisely so far as corresponds to the prematureness of the cardiac action. Thus, in this instance, a compensatory pause following a prematurely occurred extrasystole does not lead to a count pulse.

In FIG. 2, in the first line, a schematic EKG is indicated from which, by means of an R-serration-discriminator 1, square-wave pulses (shown at A) are derived, and from which, by means of monostables 2 and 3, chronologically offset trigger pulses are derived (as shown at B and C). Line D shows, as analog signal, the sawtooth voltage of the capacitor 5. In the following composite line (E,G, FIG. 2), the stored mean value voltages at the circuit point E in FIG. 1; i.e., before the amplifier 12, and at circuit point G; i.e., after the amplifier 12, are illustrated. If no output signal is transmitted by the comparator 26 (waveform K), these signal voltages E and G progress equally. In the case of omission of an event (or occurrence) in the EKG signal (as is symbolically indicated by the dash waveform in the first line designated EKG of FIG. 2), the adjusted sawtooth voltage F intersects the signal voltage G. At this timepoint, an output signal is generated as indicated at H, FIG. 2, at the output of the comparator 14 and hence a count pulse is triggered. An asystolia, or "missed beat", respectively, is displayed on the associated display apparatus.

In the normal instance (in the absence of the below mentioned circuit feature), with a compensatory pause after a double signal, a count signal would likewise be triggered. However, in this instance, through connection of the signal of the adding amplifier 27 through the comparator 26 (corresponding to waveform K) the signal at the input to comparator 14 (waveform G, FIG. 2) is raised relative to the output of capacitor 11 (waveform E) so that there is no intersection point between sawtooth voltage F and signal G, and so that no output signal is generated by the comparator 14 and hence no count pulse is triggered. Thus, the compensatory pause is eliminated prior to the further processing and is not displayed as an asystolia or "missed beat".

The inventive method and the pertaining apparatus have been described specifically for the analysis of EKG-signal sequences. Naturally, also other periodic signal sequences; for example, EEG, blood pressure, or respiratory signals, are also correspondingly analyzable.

In summary, the illustrated embodiment specifically serves the purpose of recognition of so-called asystolias in EKG-monitoring. To this end, in each instance a measure of the duration of the preceding RR-interval of the EKG is retained (e.g. by storage of the peak value attained by the period-duration measuring saw tooth waveform D, FIG. 2) as a concomitant reference value and compared with a time integrated value (e.g. waveform E, FIG. 2) representing a mean value of the RR-interval. In this manner, an asystolia can be automatically recognized, and, in particular, can be distinguished from compensatory pauses following prematurely ocurring extrasystoles.

The mean value of the measuring voltage stored by capacitor 11 is not unduly influenced by a single premature pulse such as that which occurs in the interval "2RR" of the EKG signal in FIG. 2. Thus, the level of waveform E in FIG. 2, when the level of waveform J is subtracted therefrom in amplifier 27, will provide a signal whose magnitude is a measure of the prematureness of the prematurely occurring extrasystole. Thus, in this interval, the level of waveform G exceeds the level of waveform E in proportion to the prematureness of the premature pulse.

It will be apparent that many modifications and variations may be effected without departing from the scope of the novel concepts and teachings of the present invention.

We claim as our invention:

1. A method for the analysis of essentially periodic signal sequences, in particular physiological signals such as EKG signals or the like, said method comprising
    (a) generating a measuring voltage which changes in value in proportion to the duration of a currently occurring signal period between individual signal events,
    (b) generating a mean value signal which is a function of a mean value of the measuring voltage in the preceding signal period,
    (c) generating a further signal which is a function of the signal period duration so as to represent the degree of prematureness of a signal event which has taken place,
    (d) adjusting the mean value signal relative to the measuring voltage according to said further signal,
    (e) comparing the mean value signal with the measuring voltage after the relative adjustment thereof according to the preceding step (d), and generating a comparison signal when the measuring voltage and the mean value signal, with the relative adjustment thereof, reach a predetermined comparison relationship, the adjustment of the mean value signal relative to the measuring voltage in step (d) being such that signal pauses which are brought about solely due to a prematurely occurring signal event do not result in the generation of a comparison signal, and
    (f) transmitting a missing-individual-event-recognition signal in response to the comparison signal so as to indicate missing individual signal events in the essentially periodic signal sequence while signal pauses which are brought about solely due to prematurely occurring signal events do not lead to the transmission of a missing-individual-event-recognition signal.

2. A method according to claim 1, wherein the mean value signal is increased in magnitude from an initial value in proportion to the degree of prematureness of a signal event representing the occurrence of an extrasystole in an EKG signal sequence, so that the transmission of missing-individual-event-recognition signals is an accurate measure of the occurrence of asystolias in the EKG signal sequence.

3. A method according to claim 1, wherein the mean value signal is increased in magnitude from an initial value to an adjusted value in response to the occurrence of said further signal, the further signal being generated by comparing a peak value of the measuring voltage during each signal period with an initial value of the mean value signal, the mean value signal being adjusted in response to the occurrence of said further signal in proportion to the difference between the initial value of the mean value signal and a signal proportional to said peak value when the initial mean signal exceeds such peak value.

4. A method for analyzing an EKG signal sequence, said method comprising
    (a) generating a measuring signal which changes its value in proportion to the duration of a currently occurring signal period, and recycles in response to each signal event representing the beginning of each successive signal period of the essentially periodic signal sequence corresponding to the mean heart rate,
    (b) forming a mean value signal which is a function of the time integral of the measuring signal of the preceding signal periods,
    (c) generating a further signal which is a function of the signal period duration so as to represent the degree of prematureness of an extrasystole in the EKG signal sequence,
    (d) adjusting the mean value signal relative to the measuring signal according to said further signal,
    (e) comparing the means value signal with the measuring signal after the relative adjustment thereof according to the preceding step (d), and generating a comparison signal when the measuring signal and the mean value signal, with the relative adjustment thereof, reach a predetermined comparison relationship, the adjustment of the mean value signal relative to the measuring signal in step (d), being such that signal pauses due to a prematurely occurring extrasystole do not result in the generation of a comparison signal, and
    (f) transmitting an asystolia-recognition signal in response to the comparison signal so that asystolias are indicated while premature extrasystoles do not lead to the transmission of an asystolia-recognition signal.

5. A method according to claim 4, wherein the measuring signal is compared with a preselectable constant voltage value so as to determine a fixed time duration of a signal period which is interpreted as an asystolia.

6. A method according to claim 4, with the further signal being generated by comparing a peak value of the measuring signal with a sample of the mean value signal.

7. A method according to claim 6, with the mean value signal being adjusted relative to the measuring signal in proportion to the difference between the sample of the mean value signal and a value in accordance with the peak value signal when the sample of the mean value signal exceeds such peak value signal.

8. Apparatus for the analysis of essentially periodic signal sequences of individual signal events, in particular physiological signals such as EKG signals or the like, said apparatus comprising
    (a) measuring voltage generating means for generating a measuring voltage which changes in value in proportion to the duration of a signal period between individual signal events, (b) mean value generating means for generating a mean value signal which is a function of a mean value of the measuring voltage, (c) further signal generating means for generating a further signal which is a function of the signal period duration so as to identify a prematurely occurring signal event, (d) adjusting means responsive to said further signal to adjust the mean value signal relative to the measuring voltage, (e) comparison means for comparing the mean value signal with the measuring voltage after the relative adjustment thereof by said adjusting means, and operable for generating a comparison signal when the measuring voltage and the mean value signal, with the relative adjustment thereof, reach a predetermined comparison relationship, the adjustment of the mean value signal relative to the measuring voltage by said adjusting means being such that signal pauses which are brought about solely due to a prematurely occurring signal event do not result in the generation of a comparison signal, and (f) indicating means for transmitting a missing-individual-event recognition signal in response to the comparison so as to indicate missing individual signal events in the essentially periodic signal sequence while signal pauses which are brought about solely due to prematurely occurring signal events do not lead to the transmission of a missing-individual-event recognition signal.

9. Apparatus according to claim 8, with said mean value generating means comprising a mean value circuit (8, 10) and a mean value storage (9, 11) connected with said mean value circuit for storing a mean value signal, said comparison means comprising a comparator means (14) for comparing the mean value signal stored in the mean value storage circuit with the measuring voltage.

10. Apparatus according to claim 8, with said measuring voltage generating means, comprising a capacitor (5) sng a constant current source (6) for charging said capacitor, and means (1–4) operable for the recognition of significant signal events for discharging said capacitor upon expiration of each signal period (RR).

11. Apparatus according to claim 10, characterized in that the mean value circuit is a low pass filter formed from resistance means (8) and capacitance means (10), said mean value storage comprising a controllable switch (9), and an additional capacitor (11) connected via the controllable switch (9) with said low pass filter.

12. Apparatus according to claim 8, with measuring voltage adjustment means for adjusting the measuring voltage comprising voltage divider means (15 through 18) and control switches (19 through 21) connected therewith and selectively operable for controlling the value of adjusted measuring voltage transmitted thereby.

13. Apparatus according to claim 8, with a comparator (22) for comparing the measuring voltage with a constant voltage, said comparator being coupled with an input of said comparison means and being responsive to a predetermined comparison relationship between said measuring voltage and said constant voltage to reverse the polarity of said input of the comparison means (14) so that the comparison means (14) transmits said recognition signal.

14. Apparatus according to claim 8, with further comparison means (26) for comparing an adjustable peak value of the measuring voltage with a stored mean value and being responsive to a specifiable comparison relationship therebetween to connect an additional voltage to the first-mentioned comparison means (14).

15. Apparatus according to claim 14, with peak value storage means including sample-and-hold circuits (29, 30, 31, 32) and voltage divider means (33, 34) connected in series between said measuring voltage generating means and an input of said further comparison means for supplying an adjusted measure of the peak value of the measuring voltage thereto.

16. Apparatus according to claim 14, with an adding amplifier (12) connected with said first-mentioned comparison means (14) for the purpose of increasing mean value signal supplied to the first-mentioned comparison means (14), the additional voltage being added via the adding amplifier (12) connected with the first-mentioned comparison means (14).

17. Apparatus according to claim 14, with means for supplying the additional voltage being responsive to the peak value of the measuring voltage and comprising a sample-and-hold circuit (31, 32) connected with an input of said further comparison means (26).

18. Apparatus according to claim 17, with the additional voltage supplying means having an amplifier (27) responsive to the mean value signal and the peak value signal and thereby to the prematureness of the significant event.

* * * * *